(12) United States Patent
Stephens

(10) Patent No.: US 6,224,586 B1
(45) Date of Patent: May 1, 2001

(54) POSITIONING DEVICE

(75) Inventor: Douglas N. Stephens, Davis, CA (US)

(73) Assignee: EndoSonics Corporation, Rancho Cordova, CA (US)

( * ) Notice: Subject to any disclaimer, the term of this patent is extended or adjusted under 35 U.S.C. 154(b) by 0 days.

(21) Appl. No.: 09/391,071

(22) Filed: Sep. 4, 1999

(51) Int. Cl.$^7$ ................................................ A61M 25/00
(52) U.S. Cl. ........................ 604/523; 604/160; 604/264
(58) Field of Search .................................. 604/523, 533, 604/534, 535, 538, 539, 905, 264, 160, 536, 537, 164.05, 158, 159, 161, 164.01

(56) References Cited

U.S. PATENT DOCUMENTS

| | | | |
|---|---|---|---|
| 3,545,443 | * 12/1970 | Amsari | 604/160 |
| 3,827,434 | * 8/1974 | Thompson et al. | 604/160 |
| 3,995,628 | * 12/1976 | Gula et al. | 604/160 |
| 4,149,535 | 4/1979 | Volder . | |
| 4,354,491 | * 10/1982 | Marbry | 604/160 |
| 4,498,902 | * 2/1985 | Ash et al. | 604/164.05 |
| 4,585,013 | * 4/1986 | Harris | 604/160 |
| 4,921,479 | 5/1990 | Grayzel . | |
| 4,929,243 | 5/1990 | Koch et al. . | |
| 5,203,774 | 4/1993 | Gilson et al. . | |
| 5,360,414 | * 11/1994 | Yarger | 604/264 |
| 5,709,661 | 1/1998 | Van Egmond et al. . | |
| 5,836,306 | 11/1998 | Duane et al. . | |
| 5,902,331 | 5/1999 | Bonner et al. . | |

\* cited by examiner

Primary Examiner—John D. Yasko
(74) Attorney, Agent, or Firm—Leydig, Voit & Mayer, Ltd.

(57) ABSTRACT

A catheter position guide (100) includes a first open channel (104) along the length of the position guide (100) designed to receive a catheter (202). An optional second channel (112) substantially on the opposite side of the first channel (104) is designed to receive a guide wire (204). One or more hubs (106, 108) help retain the catheter position guide's proximal end (110) to a pullback device (310).

10 Claims, 3 Drawing Sheets

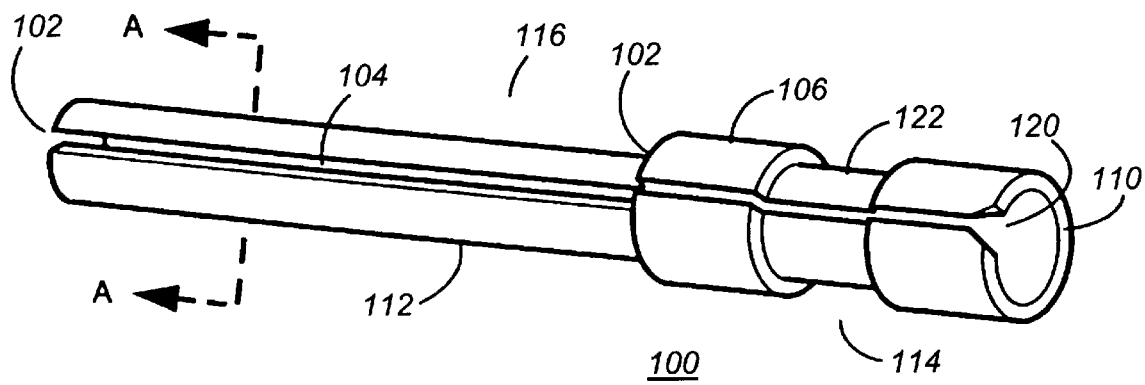
FIG. 1
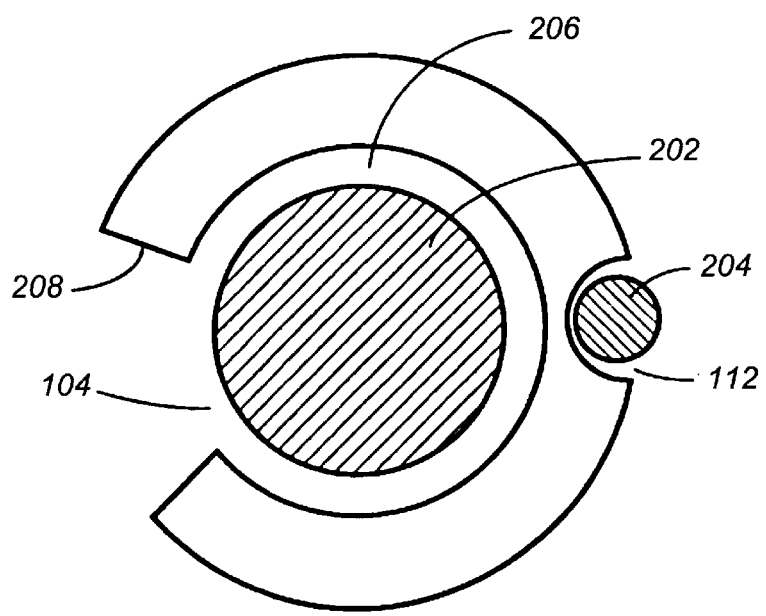
FIG. 2 SECTION A-A

POSITIONING DEVICE

BACKGROUND

When performing medical procedures using an intravascular ultrasound catheter, it is sometimes beneficial to move the catheter in a controlled manner in order to accurately characterize a lesion site. Characterization of the lesion site is performed using an ultrasound transducer mounted within the catheter, with the ultrasonic images being displayed using an external monitor which is part of the ultrasound system.

Movement of the ultrasound catheter through the lesion site is sometimes accomplished using a catheter displacement device also referred to as a "pull-back" device. A pull-back device is disclosed in U.S. Pat. No. 5,709,661, entitled "Electronic Catheter Displacement Sensor". The pull-back device can advance or retract a catheter slowly in a controlled manner through a desired location within a patient's vessel. In use, a physician advances the catheter to a site within the vessel that may be of interest and then uses the pull-back device to precisely move the catheter within the area of interest. A typical pull-back device being able to move the catheter in increments of 1.0 millimeters/second or less.

With advancements in intravascular ultrasound imaging, more precise characterizations of the lesion sites can be had, thereby increasing the ability for physicians to properly diagnose and treat a lesion site. These advancements require the precise movement and location of the catheter. Typical treatments to improvement the patency of the lesion site include the use of balloon angioplasty and when appropriate, the placement of a stent in the affected area.

A few problems currently exist when using a pullback device to control the movement of a catheter. One such problem is that currently there is no simple device which provides a relative position of the pull-back device to the introducer sheath or guide tube used to introduce the catheter into the patient. Not having such a device can affect the ability to properly determine how far a catheter has been advanced or retracted from a patient.

Another noted problem is that blood typically gets splattered over the pullback device during a procedure that may sometimes affect the operation of the device. A device, which could help redirect some of this blood away from the pullback device, would be beneficial. Additionally, in the use of a catheter without "over-the-wire" guidance, the guide wire may move from its intended fixed position in the vessel of interest while a pullback device controls the movement of a catheter. This of course could cause the physician to have to spend extra time placing the guide wire back into position during a procedure. As shown, a need exists in the art for a device that can minimize these noted problems.

BRIEF DESCRIPTION OF THE DRAWINGS

The features of the present invention, which are believed to be novel, are set forth with particularity in the appended claims. The invention, together with further objects and advantages thereof, may best be understood by reference to the following description, taken in conjunction with the accompanying drawings, in the several figures of which like reference numerals identify like elements, and in which:

FIG. 1 shows a catheter position guide device in accordance with the present invention.

FIG. 2 shows a cross-sectional view of the catheter position guide device taken along line A—A with a catheter and guide wire located in their respective channels.

DETAILED DESCRIPTION OF THE PREFERRED EMBODIMENT

Figure 3:
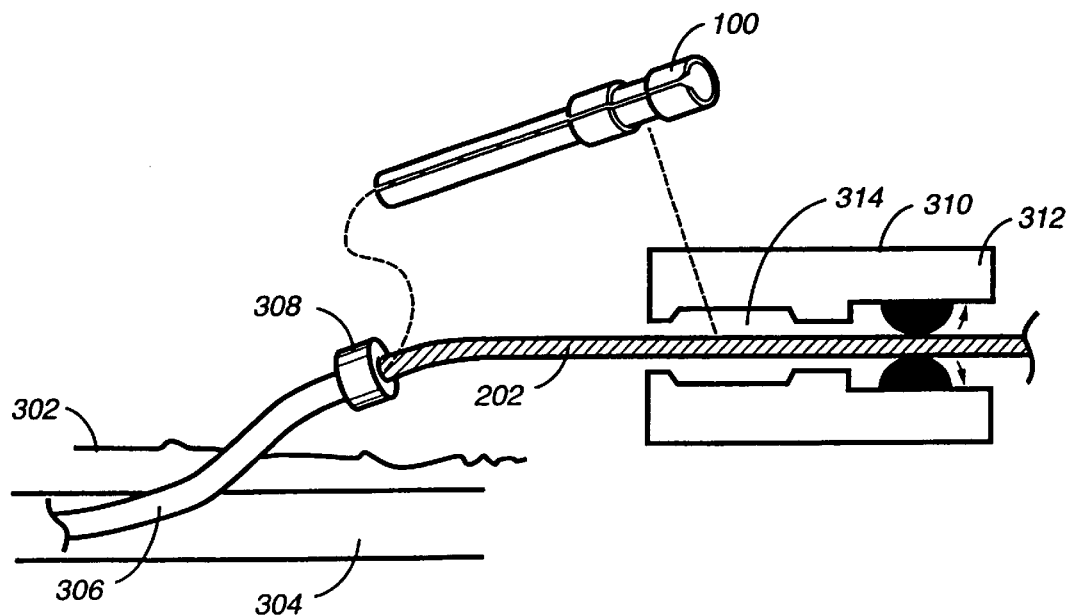
FIG. 3 illustrates how the catheter position guide is inserted into a catheter in accordance with the invention.

While the specification concludes with claims defining the features of the invention that are regarded as novel, it is believed that the invention will be better understood from a consideration of the following description in conjunction with the drawing figures, in which like reference numerals are carried forward.

Referring now to FIG. 1, there is shown a catheter position guide 100 in accordance with the preferred embodiment. The position guide 100 has a proximal end 110 and a distal end 102. In medical devices, the term proximal end is considered to be the end closest to the catheter operator, while the term distal end means the end of the device farthest from the catheter operator.

A retention means such as set of hub members 106 and 108 are located at the proximal end 110 as shown separated by a transition section 122. Hubs 106 and 108 are designed to help retain the position guide 100 to a pullback device as will be discussed below. A first or catheter open channel 104 is located along the length of the catheter position guide 100. In the preferred embodiment open channel has an opening of approximately 0.020-inch. The open channel 104 can be established by using cutting, molding, or extruding construction methods.

Channel 104 is designed to receive and guide a catheter as it exits a patient and it moves into the pull back device as will be discussed further below. An optional second or guide wire open channel 112 preferably opposite to the first open channel 104 is designed to receive a conventional guide wire. If the optional second channel 112 is used, it does not have to run the entire length of the position guide device and can terminate upon reaching the distal end 118 of hub section 114 or before. Hub section 114 includes a angled end portion 120 which helps in inserting a catheter into the open channel 104. Since a typical catheter will have a larger diameter (e.g., 0.040 inch) than the opening for the open channel 104 (0.020 inch) the sides of the opening can be pulled apart with the catheter until the catheter is fully inside of the open channel 104.

Catheter position guide 100 is preferably molded from plastic, such as PEBAX® medical grade plastic manufactured by Elf Atochem, or other well-known plastics used to make medical devices, although other materials (e.g., stainless steel, aluminum, etc.) appropriate for medical applications may also be used. The catheter position guide 100 can be designed as a single piece or designed as two pieces, a shaft or tube section 116 and the hub section 114 which are bonded together using one of many medical grade adhesives.

In the preferred embodiment the catheter position guide 100 is designed as a two piece assembly with the hub section 114 formed from white PEBAX® 4033-SA01 medical grade plastic having a durometer of approximately 40. The hub section is molded with the channel formed within it, and the sidewall is then cut to form the opening slot for the open channel 104. The tube section 116 is preferably manufactured using clear PEBAX® medical grade plastic having a durometer of approximately 60 for added stiffness. The catheter shaft 116 is extruded to form inner channel 206 and then the sidewall is cut at 208 as shown in FIG. 2 to form the open channel 104. Inner channel 206 has a diameter of approximately 0.113 inch which allows catheter 206 to travel freely along the entire length of the catheter position guide 100. Once the two pieces 114 and 116 are manufactured, they are aligned so that their open channel slots are in alignment, and the pieces are then bonded together using a medical grade adhesive.

FIG. 2 shows a cross-sectional view of the catheter position guide 100 with a catheter 202 and a guide wire 204 located in their respective open channels 104 and 112. One advantage of the catheter position guide 100 especially if the optional second channel 112 is used is that it helps keep the guide wire 204 from tangling up with the catheter 202. The size of the second open channel 112 will depend on the diameter of the guide wire 204.

Referring now to FIG. 3, there is shown an illustration of a medical system showing how the catheter position guide 100 is installed. During a typical catheterization procedure, an introducer sheath and guide catheter 306 are introduced through a patient's skin 302 and into the desired vessel 304. The proximal end of the introducer sheath includes a connector such as a Tuohy-Borst connector 308. In order to install the position guide 100 the guide is positioned so that the catheter channel 104 is aligned with catheter 202 and the catheter is pressed into the open channel 104. Next, the distal end of the position guide 100 is pressed into the connector 308. The proximal end having hubs 106 and 108 is placed within a slot 314 located within pullback device 310. In this example, the pullback device 310 used is preferably a TRAK BACK™ pullback device manufactured by Endosonics Corporation, Rancho Cordova, Calif. Pullback device 310 has a hinged top 312 which exposes slot 314, once the hub section 114 is placed in slot 314, the top section 312 of the pullback device 310 is shut.

Figure 4:
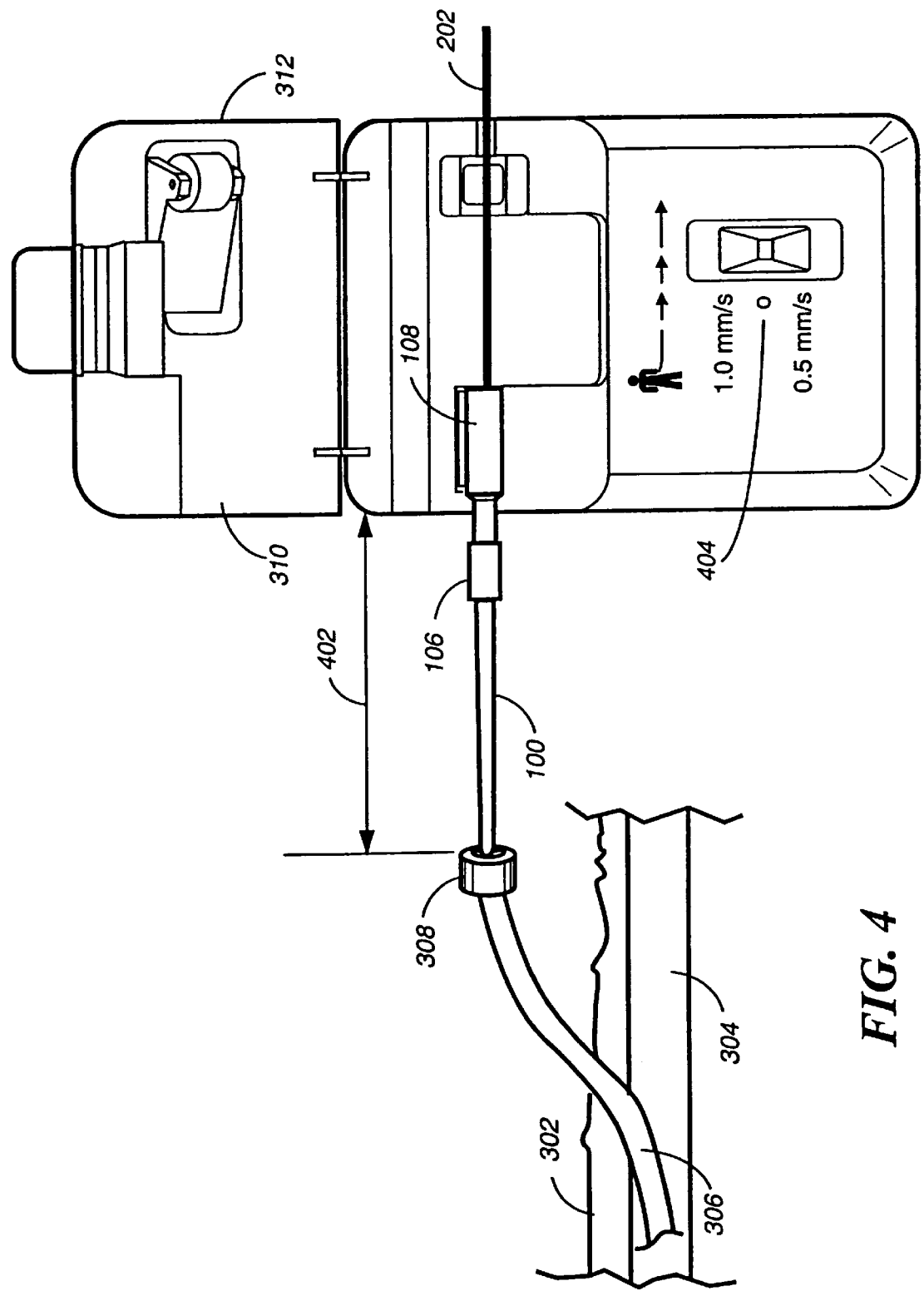
FIG. 4 shows the catheter position guide attached between a pullback device and a connector in accordance with the invention.

In FIG. 4 the pullback device 310 is shown with its top 312 in the open position. Pullback device 310 includes a switch 404 for turning on the unit and for selecting between a speed of 0.5 mm/s or 1.0 mm/s.

Once the catheter position guide 100 is installed it helps maintain a fixed distance 402 between connector 308 and the pullback device 310 as shown in FIG. 4. By maintaining a fixed distance between connector 308 and pullback device 310 a more precise pullback operation can be performed since the relative position of the pull-back device is fixed to the connector 308 and does not change during the procedure. The overall length of the catheter position guide 100 can vary depending on the particular design, but an overall length of two or three inches would be typical for most applications.

One advantage of the catheter open channel 104 is that it allows blood that leaks out of connector 308 to drip out of the channel 104 prior to reaching the pullback device 310. This helps minimize the pullback device rollers from getting saturated with blood and causing slippage of the catheter during movement.

Figure 5:
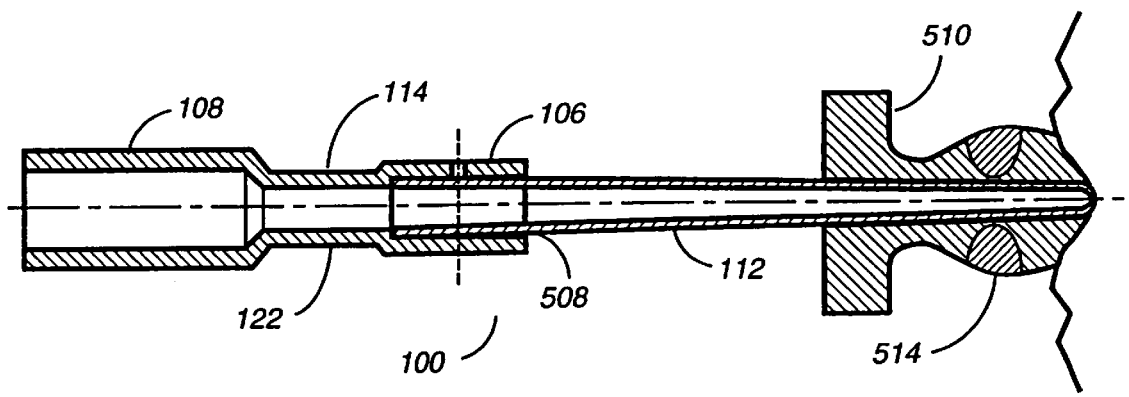
FIG. 5 shows a cross-sectional view of the catheter position guide attached to a connector.

In FIG. 5 there is shown a cross-sectional view of the catheter position guide 100 having its distal end 102 inserted into a connector such as Tuohy-Borst connector 510. The hub section 114 of the position guide 100 includes the larger proximal hub 108 that in the preferred embodiment has an outer diameter of approximately 0.295 inch and a length of approximately 0.670 inch. The smaller diameter hub 106 is located at the distal end of the hub section 104. Hub 106 has an outside diameter of approximately 0.232 inch and a length of approximately 0.410 inch. Hubs 106 and 108 are separated by the transition area 122 having a length of approximately 0.146 inch and an outer diameter of approximately 0.196 inch.

A counterbored aperture 508 having a length of approximately 0.38 inch and a inner diameter of approximately 0.146 inch is located in the smaller hub section 106 and is used for receiving the guide tube 116 which has an outer diameter of approximately 0.144 inch. Guide tube 116 is bonded using a medical grade adhesive to hub section 114.

The "C" cross-sectional shape of the tube 112 at its distal end 102 helps form a compression fit with the connector 510 once it is inserted into the connector's apperture. Connector 510 also typically will contain a sealing ring 514 such as an O-ring that helps further retain the position guide device 100. Referring back to FIG. 2, the guide wire channel 112 is preferably designed such that the guide wire 204 extends slightly outside of the channel 112. This allows for the sealing ring 514 to retain the guide wire in place between the sealing ring 514 and the guide wire channel 112. The guide wire channel 112 not only helps keep the guide wire 204 from tangling up with catheter 202, but it provides a solution in conjunction with sealing ring 514 for the problem of the guide wire being moved out of position inside of the patient while the catheter 202 is being manipulated.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as defined by the appended claims. For example, although the tube 100 has been shown having a hub section 114, in other designs for example, when the pullback device does not have a slot 314, and simply an opening like connector 5 10, the hub section 114 can be eliminated, and the proximal end of the tube can make a compression fit into the pullback device, like is done with the distal end of the tube 102 and connector 510.

What is claimed is:

1. A catheter position guide, comprising:

a tube having proximal and distal ends;

a catheter open channel running along the length of the tube for receiving a catheter; and a guide wire open channel running along at least a portion of the tube.

2. A catheter position guide as defined in claim 1, further comprising:

a hub section located at the proximal end of the tube.

3. A catheter position guide as defined in claim 2, wherein the hub section includes a distal end having a counterbore for receiving the proximal end of the tube.

4. A catheter position guide as defined in claim 1, wherein the catheter open channel is formed by extruding and cutting the tube.

5. A catheter position guide as defined in claim 2, wherein the hub section includes first and second hub members.

6. A catheter position guide as defined in claim 2, wherein the hub section also has the catheter open channel running along its length.

7. A catheter position guide as defined in claim 1, wherein the guide wire open channel is located on substantially the opposite side of the tube from the catheter open channel.

8. A medical system, comprising:
   a catheter;
   a guide wire;
   a catheter position guide, comprising:
   a tube having proximal and distal ends, the tube having a guide wire open channel running along at least a portion of the tube for receiving the guide wire;
   a catheter open channel running along the length of the tube for receiving the catheter; and
   a connector having an opening for receiving the distal end of the tube.

9. A medical system as defined in claim 8, further comprising:
   a catheter pullback device coupled to the proximal end of the tube; and
   the catheter runs through the inside of the connector and along the catheter open channel to the pullback device.

10. A medical system as defined in clam 8, wherein the connector includes a sealing ring which can retain the guide wire by pressing the guide wire between the sealing ring and guide wire open channel.

* * * * *